US011826177B2

(12) United States Patent
Peres (10) Patent No.: US 11,826,177 B2
(45) Date of Patent: Nov. 28, 2023

(54) INTELLIGENT HEADACHE MANAGEMENT SYSTEM

(71) Applicant: Mario Fernando Prieto Peres, Sao Paulo (BR)

(72) Inventor: Mario Fernando Prieto Peres, Sao Paulo (BR)

(*) Notice: Subject to any disclaimer, the term of this patent is extended or adjusted under 35 U.S.C. 154(b) by 409 days.

(21) Appl. No.: 17/196,611

(22) Filed: Mar. 9, 2021

(65) Prior Publication Data

US 2022/0110591 A1 Apr. 14, 2022

(30) Foreign Application Priority Data

Oct. 8, 2020 (BR) .................. 10 2020 020706 7

(51) Int. Cl.
*A61B 5/00* (2006.01)
*A61B 5/12* (2006.01)
(Continued)

(52) U.S. Cl.
CPC .......... *A61B 5/7282* (2013.01); *A61B 5/0002* (2013.01); *A61B 5/02055* (2013.01);
(Continued)

(58) Field of Classification Search
CPC .... A61B 2562/0204; A61B 2562/0219; A61B 5/0002; A61B 5/0022; A61B 5/0077; A61B 5/01; A61B 5/015; A61B 5/02055; A61B 5/021; A61B 5/022; A61B 5/024; A61B 5/053; A61B 5/1101; A61B 5/12; A61B 5/126; A61B 5/14542; A61B 5/14551; A61B 5/163; A61B 5/165; A61B 5/256; A61B 5/282; A61B 5/372; A61B 5/378;
(Continued)

(56) References Cited

U.S. PATENT DOCUMENTS

| 10,388,407 B2 | 8/2019 | Apte et al. |
| 2020/0013509 A1 | 1/2020 | Matharu |
| 2021/0220210 A1* | 7/2021 | Berdahl ................. A61H 7/001 |

FOREIGN PATENT DOCUMENTS

| AU | 784736 B2 | 8/2001 |
| WO | 2019207510 A1 | 10/2019 |

* cited by examiner

*Primary Examiner* — Mark D Remaly
(74) *Attorney, Agent, or Firm* — HAUPTMAN HAM, LLP (57) ABSTRACT

The present invention falls within the field of medical diagnosis, more particularly in the field of computational methods for headache diagnosis.

In short, the invention consists of an intelligent headache management system that comprises a plurality of remote modules connected with at least one analysis module, the remote modules being responsible for the collection of information related to the user and said information collection is carried out by at least one information collection device connected to said remote module. The information is transmitted to an analysis module, which comprises means to store and process the information transmitted by the remote module. The results from the computational processing of said information are transmitted to at least one remote module, being available to the user. The remote module comprises information collection devices for the collection of information actively provided by the user and for the automatic collection of information from the user and comprises stimulus devices for the emission of sensory stimuli to provoke biological responses from the user.

16 Claims, 2 Drawing Sheets

(51) Int. Cl.
  *G16H 40/67* (2018.01)
  *G16H 50/20* (2018.01)
  *A61B 5/0205* (2006.01)
  *A61B 5/01* (2006.01)
  *A61B 5/022* (2006.01)
  *A61B 5/024* (2006.01)
  *A61B 5/1455* (2006.01)
  *A61B 5/11* (2006.01)
  *A61B 5/372* (2021.01)
  *A61B 5/053* (2021.01)

(52) U.S. Cl.
  CPC .............. *A61B 5/12* (2013.01); *A61B 5/4011* (2013.01); *A61B 5/742* (2013.01); *G16H 40/67* (2018.01); *G16H 50/20* (2018.01); *A61B 5/0077* (2013.01); *A61B 5/015* (2013.01); *A61B 5/022* (2013.01); *A61B 5/024* (2013.01); *A61B 5/053* (2013.01); *A61B 5/1101* (2013.01); *A61B 5/14551* (2013.01); *A61B 5/372* (2021.01); *A61B 5/4803* (2013.01); *A61B 5/6803* (2013.01); *A61B 5/7475* (2013.01); *A61B 2562/0204* (2013.01); *A61B 2562/0219* (2013.01)

(58) Field of Classification Search
  CPC ......... A61B 5/38; A61B 5/381; A61B 5/4011; A61B 5/4803; A61B 5/4824; A61B 5/4848; A61B 5/486; A61B 5/6803; A61B 5/7267; A61B 5/7282; A61B 5/7405; A61B 5/7415; A61B 5/742; A61B 5/7475; G16H 40/67; G16H 50/20
  See application file for complete search history.

INTELLIGENT HEADACHE MANAGEMENT SYSTEM

FIELD OF APPLICATION

The present invention relates to the field of medical diagnosis, more specifically the field of computational methods for headache diagnosis.

In another embodiment, the present invention relates to the field of remote diagnosis and management systems, in particular it relates to the field of systems for headache diagnosis and management, especially systems focused on primary and secondary headaches.

BACKGROUND OF THE INVENTION

The state of the art related to medical information collection and processing systems, which includes remote systems, has already been extensively investigated. Among the many examples, a standout is the so-called Electronic Medical Record (EMR), which provide an information system with means to record, access and share medical that enables interconnection of patients, professionals and medical institutions, among other types of users.

Despite being an interesting solution regarding medical information registration, access and sharing, the EMR lacks the means to carry out computational diagnostics without intermediation of medical professionals. That is, the EMRs only increase the availability of medical information while maintaining the diagnosis dependent of a medical professional.

In view of the EMR deficiencies, several other solutions in the field of computer-assisted diagnosis, or computational diagnosis, have been proposed. Such solutions disclose diagnostic systems with the remote data collection and their greater information accessibility of EMR, adding up tools to automate the collection and processing of the data gathered. The main goal these solutions is to provide a diagnosis without mandatory intermediation of a health professional. Moreover, the data collection procedure revealed by such inventions is largely based on digital forms, which are organized by specific diagnostic criteria of each target disease. Thus, the information collected process is highly standardized, facilitating the diagnosis by computational methods.

Another drawback of computational methods result from the fact that such methods favor the collection of information through forms, losing the ability to analyze nuances, such as patient's mental and emotional state. These nuances in mental and emotional state are extremely important for a diagnosis with greater precision and quality, since the provide elements to determine the best type of treatment for each patient. The analysis and incorporation of such factors in a diagnostic process traditionally occurs through doctor-patient interaction, depending largely on the physician's professional experience and sensibility. Consequently, the elimination of the mandatory participation of a doctor in the computational diagnosis process, together with any human interaction, leads to a lack of sensitivity needed for identification and collection of data regarding the patient's mental and emotional state.

More specifically, in the case of headache diagnosis, the collection of data regarding a patient's mental state can lead to the identification of diseases and medical conditions potentially related to the origin of the headache, thus facilitating the classification and diagnosis of the headache and the delimitation of more efficient and effective treatment strategies.

Another problem of the computational diagnostic methods disclosed in the state of the art concerns the methods used for the information collection from the users, in particular those information concerning light-induced (photophobia) and noise-induced discomfort (phonophobia), which are both of great significance in headache diagnosis. Currently, the degree of phonophobia or photophobia are reported by the patient, who evaluates its own degree of discomfort within a range, usually numeric and wherein one end indicates low or no discomfort and the opposite end indicates high discomfort. Methods such as these, however, fail to standardize the information collection and may not adequately reflect the degree of discomfort experienced by the patient.

The following are some inventions that make up the state of the art:

D1 AU 784736 B2: The invention discloses a computer-assisted diagnostic methodology. In particular, the invention discloses a method for organizing patient's medical data that can be implemented in software language, enabling its effective manipulation and processing for medical diagnosis purposes. The collection of patient's information is carried out through dynamic questionnaires, each question being selected according to the previous answer, creating a dialogue. Once the patient's information has been collected and organized, the software analyses that information, providing a diagnosis. The present invention can be applied to a multiplicity of diseases, as long as their symptoms and other information are properly registered in the system.

Although D1 AU 784736 B2 discloses a computational method for remote disease diagnosis, the invention does not disclose methods of continuous automated optimization for computational diagnostic method. Furthermore, the method deals with the disease diagnosis in general, lacking any specificities for headache diagnosis.

D2 U.S. Ser. No. 10/388,407 B2: Discloses an invention relating to a system and method for medical conditions diagnosis associated with headaches. The diagnostic method is based on the microbiota assessment from different parts of the body, in order to determinate possible diseases associated with headache. In addition, the invention discloses the use of complementary information to characterize the disease associated with a headache.

The invention disclosed by D2 U.S. Ser. No. 10/388,407 B2 refers to a computational method for headache diagnosis via addition of human microbiota. Despite the fact that a specific computational method for headache diagnosis is disclosed, the solution is unable to provided means for data collection regarding the patient's mental health.

D3 WO 2019/207510 A1: The invention disclosed relates to a system, method and apparatus for neurological diseases diagnosis and treatment. The invention comprises a plurality of sensors, including sensors for image and sound capturing. According to the disclosed method, patient's medical information is combined with patient's data obtained through the plurality of sensors through methodologies involving neural networks and machine learning. Such methodologies are also used to refine the diagnostic method.

Despite disclosing a remote computational diagnostic system for neurological diseases, D3 WO 2019/207510 A1 does not discloses methods and means for standardization of data collection of some crucial information for the diagnosis of neurological diseases, in particular for primary and secondary headaches (examples include phonophobia, photophobia and odor discomforts). Thus, the diagnostic method disclosed in this document is subject to inaccuracy due to insufficient information.

D4 US 2020/0013509 A1: The invention disclosed by D4 concerns a system and method for headache diagnosis and treatment, including a diary in which the patient can record headache episodes in an organized manner. The diary is kept in a patient's repository, which comprises a processing unit and a plurality of sensors. The system generates diagnostic data for patients and health professionals, facilitating treatments and identification of potential new migraine episodes.

The invention disclosed by D4 por US 2020/0013509 A1 fails to anticipate means for standardized collection of important headache diagnosis information, including information related to photophobia, phonophobia and odor discomfort. Furthermore, the use of computational tools to enable continuous refinement of the diagnostic method and suggested treatments is not disclosed.

In view of the state of the art solutions, it is evident that there is a need for new solutions that can integrate diverse biological variables into its analyzes, including information about heartbeat, blood oxygen level, degree of photophobia, degree of phonophobia, mental state. The integration of such data with medical history data and other information about an individual's health is not an easy task, as these data differ drastically in their nature. Such challenge grasped when we observe the timid attempts to integrate biological variables documented in the state of the art. Although some inventions may have disclosed biological data integration, its is clear that even the few biological variables integrated already resulted in great challenges. In the same note, the technical problem proposed by the present invention is clearly one that emerges from critical deficiencies with highly technical challenges. To overcome this challenge, the present invention disclosed herein implements modern techniques for capturing biological variables and complex computational methods to integrate them, providing an unprecedented system that enables a more accurate diagnosis and more efficient management of headaches.

OBJECTIVES

In view of the mentioned technical problems, the present invention aims to provide an intelligent headache diagnosis system enabling a more accurate headache diagnosis for its users and a more efficient and effective headache treatments.

According to another embodiment, the present invention aims to provide an intelligent headache diagnosis system capable of remotely collecting information from users in a standardized manner, including collection of information related to phonophobia, photophobia, hand tremor, odor discomfort, among others. By doing so, the present invention also aims to collect information about the user mental health. As a result, the disclosed system enables a diagnosis with greater precision and quality and treatments with higher effectiveness.

SUMMARY OF THE INVENTION

According to a preferred embodiment, the present invention relates to an intelligent headache diagnosis system comprising a plurality of remote modules 6 connected to at least one analysis module 7, wherein said remote modules are responsible for the collection of information 3 from the user 1. Said collection of information 3 is carried out by at least one information collection device 5 connected to said remote module 6, and said information is transmitted to at least one analysis module 7, wherein said module of analysis has means to store 8 and process the information transmitted by the remote module 6. The results from the computational processing of said information are transmitted to at least one remote module 6, wherein said results are made available to the user 1. Said remote module 6 comprises information collection devices 5 for the collection of information actively provided by the user and for the automatic collection of information from the user, wherein said remote module 6 comprises stimulus devices 4 for the emission of sensory stimuli 2 in order to provoke biological responses from the user, and said biological responses are collected automatically through at least one information collection device 5.

According to an embodiment of the present invention, the information 3 from user 1 automatically collected by devices 5 connected to a remote module 6 includes at least one of the following types of information:
a) voice audio;
b) heartbeat;
c) facial and body image;
d) infrared facial image;
e) auditory impedance information;
f) blood pressure information;
g) body temperature;
h) oximetric information;
i) hand tremor;
j) electroencephalographic information.

According to another embodiment derived from the above embodiment, said remote module 6 comprises at least one of the following information collection devices 5:
a) microphone;
b) heart rate sensor;
c) digital camera;
d) infrared camera;
e) impedanciometer;
f) digital sphygmometer;
g) thermometer;
h) oximeter;
i) accelerometer;
j) helmet or cap for electroencephalogram;
k) touchscreen panel.

According to yet another preferred embodiment, said remote module 6 comprises at least one stimulus device 4 with means to emit at least one of the following types of sensory stimuli 2:
a) visual;
b) olfactory;
c) auditory;
the emission of visual stimuli is carried out by an image reproduction device; the emission of olfactory stimuli is carried out by an odor release device; and the emission of auditory stimulus is carried out by a sound reproduction device.

According to an embodiment of the present invention, the automatic collection of information 3 related to the biological response of the user carried by at least one information collection device 5 connected to a remote module 6, is immediately after the emission of sensory stimulus 2, said stimulus 2 being emitted by at least one stimulus device 4.

According to an alternative embodiment, said emitted stimulus 2 is a visual, olfactory, auditory stimulus or any combination of these.

According to another embodiment, the information 3 collected automatically after the start of stimulus emission 2 includes at least one of the following information:
a) voice audio;

b) heartbeat;
c) facial and body image;
d) infrared facial image;
e) auditory impedance information;
f) blood pressure information;
g) body temperature;
h) oximetric information;
i) hand tremor;
j) electroencephalographic information.

According to an embodiment derived from the aforementioned embodiments, the intelligent headache diagnosis system has means to quantitatively measure the degree of photophobia, phonophobia and odor discomfort, by collecting information 3 obtained by information collection devices 5 connected to a remote module 6, and means to computationally process said information in an analysis module 7. Additionally, said collected information 3 comprises information of voice audio and facial and body image, wherein said information is converted by said analysis module 7 in at least information related to voice intensity, use of language, speech pattern, facial expression and pupil dilation. Moreover, said information is transformed into numerical information and then computationally processed to assess the degree of phonophobia, photophobia and odor discomfort.

According to an embodiment of the present invention, the information received by the analysis module 7 is computationally processed, wherein said processing comprises at least the following four steps:

a) a screening step 101;
b) a headache diagnosis step 102, including a headache diagnosis module 22, said module divided into at least two distinct diagnostic submodules, a first primary headache submodule 25 and a second secondary headache submodule 23;
c) a comorbidities and associated factors assessment step 103; and
d) an access and impact assessment step 104;

the screening step involves a questionnaire on the frequency of headache episodes 20, wherein, in case of weekly frequency response greater than or equal to 15 episodes, a high severity alert 21 is triggered in the system. Additionally, the headache diagnosis step 102 involves the analysis of user information, including information actively provided by the user and information collected automatically, including information on medical history, headache history, habits and addictions, wherein the analysis of this step is divides between the two diagnostic submodules, the primary headache submodule 25 and the secondary headache diagnostic submodule 23. Moreover, the comorbidities and associated factors assessment step 103 involves the analysis of a plurality of user data, including information medical history, headache history, habits and addictions and other symptoms and pains, such analysis being carried out by the comorbidities and associated factors assessment module 31. Furthermore, the access and impact assessment step 104 involves analyzing information about access and impact and medical history, being said analysis carried out by the access and impact evaluation module 33.

According to the present invention, the analysis module 7 comprises means to store 8 and process the information collected by the remote module 6. The processing of said information involves the use of computational decision tree algorithms, wherein the result of said analysis comprises a diagnosis of at least one disease associated with a probability that, in turn, is associated with the reliability of said diagnosis and the recommendation of at least one medical treatment associated with its effectiveness in the treatment of said diagnosed disease, and that treatment is chosen from those stored in a treatment database 8 of an analysis module 7.

According to an embodiment of the present invention, the computational processing performed by the analysis module 7 uses at least one decision tree algorithm.

According to an alternative embodiment, the decision tree algorithm used comprises at least one of the following types of algorithm: bootstrap, bootstrap aggregation, random forest, and markov.

According to the same embodiment, the information collection procedure performed by remote module 6 and the decision tree algorithm performed by analysis module 7 are constantly optimized through the implementation of computational tools based on machine learning and neural networks.

DETAILED DESCRIPTION OF THE INVENTION

The present invention discloses an intelligent headache management system with means to remotely carried out information collection from a user and processing said information. As a result, the system classifies headache and provides at least a headache diagnosis and at least a treatment for said headache.

The intelligent headache management system disclosed herein comprises a plurality of remote modules, which function as the main user interface. By using said remote modules the system collects information from the user, communicates diagnosis and provides a channel to request or submit information into the system. The information collected by a remote module is transmitted to an analysis module, which is responsible for the storage and computational processing of said information. The computational processing carried by the remote module provides the user with at least one headache diagnosis and at least one treatment option for said headache. In order to constantly improve the accuracy and reliability of the diagnosis and the effectiveness of the suggested treatments, the computational processing (including its various steps, parameters, variables and algorithms) is subjected to continuous optimizations supported by tools such as machine learning and neural networks.

Within the scope of the present invention, the term "remote module" refers to a computer or any other form of device comprising means to collect, store, process and transmit information over a computer network. In the context of the present invention, a remote module can assume a plurality of configurations, including: smartphones, tablets, notebooks, desktops and digital totems.

According to a preferred embodiment of the invention, the intelligent headache management system comprises a plurality of remote modules, which are connected to at least one analysis module. The connection between the different remote modules and the analysis module can be achieved in several ways, preferably through network connections, including virtual private network connections (VPN), local (LAN), metropolitan (MAN), regional (RAN) or worldwide (WAN), preferably via WAN, more preferably via the internet.

According to a preferred embodiment of the present invention, the remote module comprises a plurality of information collection devices, which are connected to said remote module through wired connections, including USB 2.0, USB 3.0, USB 3.1, USB 3.2 connections, USB 4.0, and their respective variants of cables A, B and micro, coaxial cable, VGA cable, fiber optics, or wireless connections, including connections such as Bluetooth, wireless and near faith communication (NFC). The connection of said information collection devices with said remote module is detachable, allowing the same information collection device to connect to different remote modules, wherein said device may be connected to one or more remote modules simultaneously. Alternatively, such information collection devices are embedded in the structure of the remote module itself.

According to the present invention, a remote module comprises at least one of the following information collection devices: microphone; heart rate sensor; digital camera; infrared camera; impedanciometer; digital sphygmometer; thermometer; oximeter; hand accelerometer; helmet or cap for electroencephalogram. Preferably, a remote module comprises at least the devices: microphone; heart rate sensor; digital camera; thermometer; oximeter; accelerometer. Alternatively, said remote module comprises all mentioned devices.

The term "microphone" means: any device with the means to capture mechanical sound waves and transmit such information to a remote module through wired or wireless transmission. Within the scope of the present invention, the microphone-type device can take various forms, including built-in microphones and attachable to a remote module, and microphones based on various sound capture technologies, including condenser, electric condenser, dynamic, piezo-electric and optical fiber.

The term "heart rate sensor" means: any device with the means to measure a person's heart rate and transmit that information to a remote module via wired or wireless transmission. Within the scope of the present invention, such a heartbeat sensor may take different forms, including bracelet, band around the chest, ring, anklet, adhesive electrode.

The term "digital camera" means: any device with the means to capture images, convert said images into digital data and transmit such data to a remote module through wired or wireless transmission. Within the scope of the present invention, a digital camera type device can take several forms, including webcam, camera embedded in the remote module, amateur camera, semi-professional camera, professional camera, camera based on capture by charge coupled device (CCD) and/or by complementary metal oxide semiconductor (CMOS), camera with different analog and digital zoom capabilities and the most diverse resolutions in megapixels, camera with and without internal memory.

The term "infrared camera" means: any device with means to capture infrared images, convert said images into digital data and transmit such data to a remote module through wired or wireless transmission. Within the scope of the present invention, an infrared camera type device can take many forms, including a camera embedded in a remote module and camera attachable to a remote module.

The term "impedanciometer" means: any device with the means to measure a person's hearing capacity, convert that information into digital data and transmit that data to a remote module through wired or wireless transmission. An impedance meter must have means to emit sounds of pure frequencies, that is, sounds that have only a single frequency; sounds of different timbres, that is, sounds with different frequency positions; and sounds with different volume, that is, with different sound intensities.

By the term "digital sphygmometer" means: any device with the means to measure a person's blood pressure, convert such information into digital data and transmit such data to a remote module via wired or wireless transmission.

The term "thermometer" is intended to mean: any device with the means to measure a person's body temperature, convert that information into data and transmit that data to a remote module through wired or wireless transmission. Within the scope of the present invention, a thermometer can take many forms and be based on various technologies, including bimetallic thermometers, gas thermometers, infrared thermometers and mercury thermometers.

The term "oximeter" is intended to mean: any device with the means to measure the amount of oxygen in a person's blood, convert that information into digital data and transmit that data to a remote module through wired or wireless transmission. The measurement of oxygen levels in an oximeter is done indirectly by assessing the absorption of specific wavelengths at the ends of a person's body, usually at the fingertips. Within the scope of the present invention an oximeter may take different forms, including finger, wrist and ankle oximeters, and may use technologies based on the analysis of light absorption, as described, or other technologies.

The term "accelerometer" means: any device with the means to measure a person's hand movements, convert such information into digital data and transmit such data to a remote module through wired or wireless transmission. In particular, the accelerometer used in the present invention must be able to detect tremors from a patient's limbs, in particular the hands. Within the scope of the present invention, an accelerometer can take several forms, including pulse accelerators, ring, other forms of coupling to a person's body, particularly in the hand region.

The term "helmet or cap for electroencephalogram" means: any device with means to measure fluctuations in the electric field in a person's brain, convert such information into digital data and transmit such data to a remote module through transmission with or wireless. Within the scope of the present invention, an electroencephalogram cap or helmet can take different forms, including helmets with different numbers of electrodes, and the location of said electrodes may be chosen following specific system guidelines such as the electroencephalography 10-20, including also different formats cap and helmet, which may be composed of plastic and/or metallic materials.

The term "touchscreen panel" means: any device with the means to collect the movements of a person's body, in particular the movement of a person's fingers, through contact of the person's body with a sensed surface of a panel, and convert such information into data that can be transmitted to a remote module via wired or wireless transmission. Within the scope of the present invention, a touchscreen panel can take different forms, including panels coupled to image reproduction devices, panels in different formats and sizes, such as panels designed for mobile phones, tablets, digital totems and other electronic devices, such panels being able to be embedded in a remote module.

According to an alternative embodiment of the present invention, two or more information collection devices can be presented as a single device, as would be the case with a device comprising a microphone and a digital camera.

Within the scope of the present invention, any of the aforementioned devices can be an independent device with means to communicate with a remote module via wired or wireless connection, or it can be a device embedded in a remote module.

According to yet another alternative embodiment of the present invention, the information collection carried out by a given information collection device may be executed by a device not connected to a remote module. In this case, said device may be handled by a user who, after performing the reading or measurement of given information from the user with said device, may manually enter the value indicated by the device in the remote module via a digital form, which may involve answering a written questionnaire, a multiple-choice questionnaire or orally reporting the information. Thus, a given user can choose to couple a small number of information collection devices to a remote module, since there is the possibility to supplement the information with other devices not necessarily connected to the remote module. In other words, the choice of which devices will be connected to a remote module and the way in which they will be connected (by wired or wireless connection) may vary to better adapt the use of the present invention to particular situations.

Using said information collection devices connected with a remote module, the system is able to collect a plurality of information from the user, said information may be actively provided by the user himself, either through oral means, writing, response multiple choice questionnaires, among other forms involving the emission of sound or image; or the information may be automatically collected from the user without the user actively providing it. The use of the term "actively" here is intended to indicate that the user is responsible for consciously informing a response upon request from the system.

According to the present invention, among the information collected which were actively provided by the user are included: personal information, demographic information, information on medical history, habits and addictions, headache history, access and impact, pain and other symptoms. The collection of said information may be carried out in several ways, including answering a questionnaire or filling a digital form presented by the remote module, wherein said questionnaire or digital form may include multiple choice questions, and written or oral questions. Alternatively, information can be actively provided by the user through digital documents or digitization of physical documents, such as identity cards, medical reports, clinical exam results and any other document that may contains information requested by the system.

According to the preferred embodiment of the present invention, the digital questionnaires and forms will be made available to the user preferably in the form of an image, through an image reproduction device, such as, for example, an OLED or LCD screen, connected to a module remote. Alternatively, said questionnaires and digital forms may be made available in the form of audio, wherein said audio is emitted by an sound reproduction device connected to said remote module. Said questionnaires and digital forms may be made available as an audio or image (provided through an image reproduction device) simultaneously or individually.

According to the same preferred embodiment above, once the questionnaires and forms are made available, the user can choose to provide the requested information in various ways, including written texts, multiple choice questions or speech. In the case of providing information by written text or multiple-choice questions, the remote module will collect the information through a touchscreen panel, preferably attached to an image reproduction device, connected to said remote module. In case the user chooses to provide the information by speech, the information provided will be collected by the remote module through a microphone type device. The collected audio being immediately converted into written text by computational processing carried out by the remote module itself or by the analysis module using transmission of audio information collected by the remote module.

According to the present invention, the system requests, through the remote module and its devices, a plurality of user information, including information for the purposes of user registration; diagnosis of diseases, in particular headache; suggestion of medical treatments; monitoring the evolution of the disease and the effectiveness of the suggested treatment. To facilitate information collection, the present invention provides several collection modalities, including collection by questionnaires and forms, which can be answered via interaction with a touchscreen panel or by speech collected by microphone. In the case of interaction with a touchscreen panel, according to an embodiment of the present invention, the system will provide different ways to answer questions and request information, including an expandable 2D or 3D model of the human body enabling collection of location of pain information, sliding bars enabling indication of pain intensity within a numeric range, multiple choice questions, checkbox lists to include types of symptoms associated with headache, matrix questionnaire and heat map.

Within the scope of the present invention, personal information includes: Full name, valid personal ID, fingerprint, email, cell phone.

Within the scope of the present invention, demographic information includes: age, gender, color, marital status, employment status, income, type of housing, census sector, nationality, social class, education, religiousness.

Within the scope of the present invention, medical history information includes: medications in use; health diagnosis; weight, height, BMI, mental health diagnoses; allergies, hormonal profile; metabolic profile; digestive profile; history of medical interventions and procedures.

The term "health diagnosis" refers to the set of diagnoses and symptoms associated with a person's mental illness, including diagnoses associated with traumatic events, anxiety, depression, compulsion, attention deficit, hyperactivity, personality, optimism, pessimism. According to the present invention, the user can actively inform past diagnoses associated with mental health and/or said information can be inferred by the system itself, through computational processing of information collected from the user performed by the analysis module, in particular through processing information that includes: voice intensity, use of language, speech pattern, facial expression and pupil dilation.

The term "hormonal profile" refers to the personal history of diseases, conditions or characteristics related to the endocrine system.

The term "metabolic profile" refers to the personal history of diseases, conditions or characteristics related to the circulatory and metabolism system.

The term "digestive profile" refers to the personal history of diseases, conditions or characteristics related to the food system of absorption and digestion of substances ingested by the body.

Within the scope of the present invention, information on habits and addictions includes: sleep quality; habits related to sleep and rest; use of drugs; alcohol consumption; smoking; food; physical activity.

The term "physical activity" indicates the habits and routines associated with the practice of physical activity, said information being preferably obtained through standardized questionnaires such as the international physical activity questionnaire IPAQ.

Within the scope of the present invention, information on headache history includes: date of first crisis; previous diagnoses for primary headache; acute headache treatments; preventive treatments for headache; headache-related comorbidities; medical examinations related to headache; location, intensity, duration and type of pain in past headache episodes; phenomena associated with headache; triggers related to headache; prodromes associated with headache; worsening and improvement factors associated with headache.

In the context of the present invention, the term "comorbidities" indicates: diseases that cause symptoms similar to those experienced by users suffering from headache, and such comorbidities may be of a physiological or psychological character. Some examples of headache-related comorbidities are: anxiety, depression, mania, phobias, trauma, attention deficit and hyperactivity, substance use, rhinitis, allergies, cardiovascular diseases, epilepsy, tremor, dementia, Parkinson's, sleep disorders.

In the context of the present invention, the term "phenomena associated with headache" indicates simultaneous occurrences, prior or subsequent to pain such as physiological changes, nausea, vomiting, photophobia, phonophobia, osmophobia, diarrhea, tearing, red eye, edema, obstruction nasal, runny nose, dizziness, cognitive impairment, fatigue.

In the context of the present invention, the term "triggers related to headache" indicates factors that have been observed to cause, provoke headache attacks, which may be environmental, food, mental, hormonal, professional and sleep.

In the context of the present invention, the term "prodromes associated with headache" indicates symptoms experienced by a person who anticipate an episode of headache. Prodromes are also called "first symptoms" or "signal announcements". Some examples of prodromes associated with headache include: repetitive yawning, euphoria or exaggerated energy, restlessness, irritability, anxiety, photophobia and phonophobia.

Within the scope of the present invention information on access and impact includes: degree of disability; access to health insurance, presenteeism and absenteeism.

Within the scope of the present invention information on other symptoms and pains includes: other pains experienced in the body;

According to a preferred embodiment of the present invention, the remote module is also capable of automatically collecting user information. The capture of such information takes place through information collection devices, especially through devices such as digital camera, microphone, infrared camera, heart rate sensor, accelerometer. Information automatically collected, according to the preferred embodiment of the present invention, includes at least one of, alternatively all, the following types of information: voice audio; heartbeat; facial and body image; infrared facial image; auditory impedance information; blood pressure information; body temperature; oximetric information; hand tremor; electroencephalographic information and bioimpedanciometry information. It is worth mentioning that the user may choose to manually enter some of the information mentioned above, such as blood pressure and heart rate information.

In the context of the present invention, the term "voice audio" indicates: audio information from a user and collected by a microphone-type device connected to a remote module. Said audio information coming from a user's voice can take many forms, including sounds produced by the voice in the form of speech, laughter, sneezing, grunting, whispering, yawning, shouting and any other form of sound emission through the human vocal apparatus. According to the preferred embodiment of the present invention, the audio information from the voice is indirectly used in the headache diagnosis method. Such information goes through computational processing, preferably carried out by the analysis module, generating adequate information to determine a diagnosis through the present system, including the generation of information about voice intensity, speech pattern, use of language, such information is later processed by the analysis module to assess a user's mental health and emotional state, including methods such as Latent Semantics Analysis (LSA).

In the context of the present invention, the term "heartbeat" indicates: information related to a user's heartbeat collected by a heartbeat sensor device coupled to the body of said user and connected to a remote module. Such information can be captured in the form of readings related to the field and electrical potential associated with a user's heartbeat. The computational processing of such information, preferably performed by the analysis module, generates information about the heartbeat and its fluctuations.

In the context of the present invention, the term "facial and body image" indicates: images of a user's face, body, or part thereof, collected by a digital camera-type device connected to a remote module. The information collected by said device includes information stored in the form of image and video with variable resolutions and durations.

In the context of the present invention, the term "infrared facial image" indicates: images of a user's face captured by an infrared camera-type device connected to a remote module. Such images can be computationally processed, preferably by an analysis module, resulting in a facial thermography.

In the context of the present invention, the term "hearing impedance information" indicates: information about a user's hearing capacity collected through an impedance device, also known as an impedanciometer. It is worth mentioning that, said information can be used to assess the user's hearing thresholds, assessing the hearing capacity and sensitivity and also identify any discomforts regarding specific types of sound (specific in terms of intensity, frequency and timbre). Said assessment is commonly known as audiometry.

In the context of the present invention, the term "bioimpedanciometry information" indicates: information about the proportions of a user's muscle, fat, mineral and liquid mass collected through an impedancemeter.

In the context of the present invention, the term "blood pressure information" indicates: information related to a user's blood pressure collected through a digital sphygmomanometer device connected to a remote module.

In the context of the present invention, the term "body temperature" indicates: information about a user's body temperature collected by a thermometer-type device connected to a remote module.

In the context of the present invention, the term "oximetric information" indicates: information related to a user's blood oxygen level collected by an oximeter-type device connected to a remote module.

In the context of the present invention, the term "hand tremor" indicates: information related to a user's hand movements collected through an accelerometer-type device attached to a user's hand region and connected to a remote module.

In the context of the present invention, the term "electroencephalographic information" indicates: information related to the potential and electric field of a user's brain collected through a cap-like or helmet-like electroencephalography device connected to a remote module.

According to the present invention, the automatic collection procedure varies depending on the type of information to be collected. Automatic collection includes continuous, periodic and sensory stimulus dependent collection formats. Continuous collection, as the name suggests, involves the continuous collection of information throughout user's interaction with the remote module. Periodic collection consists of collecting information during pre-defined time intervals separated by pre-defined time gaps or by means of events, such as, for example, the completion of the information collection questionnaire. In turn, the collection of information dependent on sensory stimuli, occurs only after the remote module emits some type of sensory stimulus through its stimulus devices, provoking a biological response from the user.

The choice regarding which type of automatic information collection will be used for each type of data automatically collected is variable, and it can be readjusted and optimized to improve the quality of information obtained, and consequently the quality of the resulting diagnosis and effectiveness of the treatment suggested.

Regarding the information collections associated with sensory stimulus, it is necessary to coordinate the operation of an information collection devices with a second type of device, the stimulus devices. In the context of the present invention, "stimulus devices" are: devices that generate sensory stimuli aiming to provoke some biological response in the user, including visual stimulus emitted by an image reproduction device, olfactory stimulus emitted by an odor release device and auditory stimulus emitted by audio reproduction device. The term "biological response" indicates: any physiological changes in the user proved by the sensory stimulus, including emission of sounds, screams, hand tremor, alteration of facial or body temperature, alteration of facial expression, dilation of pupils, alteration of heartbeat, and any other information related to the physiological, behavioral or mental alteration that can be captured by information collection devices or derived from said information through computer analysis.

According to the preferred embodiment of the present invention, a remote module comprises at least one of the following stimulus devices: image reproduction device, odor release device and audio reproduction device; wherein said device may emit a visual, olfactory and auditory stimuli, respectively. Said devices may be attached to a remote module through wired connections, including USB 2.0, USB 3.0, USB 3.1, USB 3.2, USB 4.0 connections, and their respective variants of A, B and micro cables, coaxial cable, VGA cable, fiber optics, and wireless connections, including Bluetooth, wireless and near faith communication (NFC) connections. Alternatively, the connection of said stimulus devices with said remote module is detachable, allowing the same stimulus device to be disconnected and connected with different remote modules, wherein said device may be connected to one or more remote modules simultaneously. Alternatively, such stimulus devices may be embedded in the structure of the remote module itself.

In the context of the present invention, the term "image reproduction device" refers to: any electronic device with the means to reproduce images making them visible to the human eye. The term also refers to devices with Liquid Crystal Display (LCD), In-Plane Switching (IPS) and Organic Light-Emitting Diode (OLED) displays. The shape and size of such devices can be determined to best suit the dimensions of a remote module to which it connects or even according to the needs of a specific application. Said image reproduction device must have means to emit different intensities of light, being preferably capable of reproducing RGB colors.

In the context of the present invention, the term "odor release device" refers to: any device with means to store specific odor substances in stable conditions in a hermetically sealed manner, the release of said substance, and consequently the odor associated with it, is controlled by the user. Said device is preferably small in size, with the capacity to store up to 5 ml, preferably at least 0.5 ml, and its size may vary according to the specific needs of an application. Its composition material is preferably plastic, alternatively being composed of metal, glass, rubber, polymeric materials or any combination of the previous options. Said device has the capacity to store substances in its gaseous, liquid, solid form or any combination of these, without significant substance loss over time.

In the context of the present invention, the term "audio reproduction device" refers to: any device with the means to reproduce audio. Said device can take many forms, including devices with speakers and speaker system, headphones or earphones.

According to an alternative configuration of the present invention, two or more stimulus devices can come together in the form of a single device, for example, a device that comprises means for both image and sound reproduction.

According to a preferred embodiment, the information collection for the evaluation of photophobia, phonophobia and odor discomfort is performed through an automatic collection procedure through sensory stimulus.

According to the present invention, an automatic information collection procedure for the assessment of photophobia involves a first emission of visual stimulus towards the user and, as soon as the emission starts, the initiation of information collection regarding the biological response from the user. The visual stimulus is emitted by a stimulus device, particularly an image reproduction device, which is connected with a remote module, either by wired or wireless connection. According to the present invention, said stimulus emitted by the image reproduction device may assume different forms, including stimuli containing images, videos, colors, and may even vary with respect to light intensity, reproduction speed, contrast, brightness and duration. Once the emission of the visual stimulus starts, the remote module begins to automatically collect information regarding the biological response provoked in the user, including at least one of the following information: voice audio; heartbeat; facial and body image; infrared facial image; auditory impedance information; blood pressure information; body temperature; oximetric information; hand tremor; electroencephalographic information; preferably the remote module begins to automatically collect information regarding the biological response provoked in the user, including, at least, the following information: voice audio; heartbeat; facial and body image; hand tremor; even more preferably, the remote module begins to automatically collect information regarding the biological response provoked in the user, including at least the following information: voice audio and facial image.

According to the present invention, an automatic information collection procedure for the assessment of phonophobia involves a first emission of auditory stimulus towards the user and, as soon as the emission starts, the initiation of information collection regarding the biological response from the user. The auditory stimulus is emitted by a stimulus device, particularly an audio reproduction device, which is connected to the remote module, either by wired or wireless connection. According to the present invention, said stimulus emitted by the audio reproduction device may assume different forms, including pure wave stimuli and timbres of multiple frequencies, which may also vary in duration, intermittency, timbre, frequency and volume. Once the emission of the auditory stimulus starts, the remote module begins to automatically collect information regarding the biological response provoked in the user, including, at least, one of the following information: voice audio; heartbeat; facial and body image; infrared facial image; auditory impedance information; blood pressure information; body temperature; oximetric information; hand tremor; electroencephalographic information; preferably the remote module starts to automatically collect information regarding the biological response provoked in the user, including, at least, the following information: voice audio; heartbeat; facial and body image; hand tremor; even more preferably, the remote module begins to automatically collect information regarding the biological response provoked in the user, including at least the following information: voice audio and facial image.

According to the present invention, an automatic information collection procedure for evaluating odor discomfort involves a first emission of olfactory stimulus towards the user, and as soon as the emission starts, the collection of information about to the biological response provoked in the user. According to the present invention, said stimulus emitted by the odor releasing device can take various forms, including stimuli composed of odor from a pure molecule or substance and odor from a composition containing multiple substances, and such stimuli may still vary in time release, substance(s) associated with the odor and odor intensity. Once the emission of the olfactory stimulus starts, the remote module begins to automatically collect information regarding the biological response provoked in the user, including at least one of the following information: voice audio; heartbeat; facial and body image; infrared facial image; auditory impedance information; blood pressure information; body temperature; oximetric information; hand tremor; electroencephalographic information; preferably the remote module starts to automatically collect information regarding the biological response provoked in the user, including, at least, the following information: voice audio; heartbeat; facial and body image; hand tremor; even more preferably, the remote module begins to automatically collect information regarding the biological response provoked in the user, including at least the following information: voice audio and facial image.

It is important to note that, through the implementation of the information collection methods disclosed herein, it is possible to collect information in a diversified way, enabling collection of information not collected by remote computational diagnostic systems disclosed in the state of the art. The present invention enables the capture and inference of information related to the use of language, emotional state, mental state and degree of photophobia, phonophobia and odor discomfort. In doing so, the diagnostic results and treatments suggested increase in reliability and effectiveness, which sets the present invention as a system with improved performance over to the inventions disclosed in the state of the art.

According to the present invention, the information collected by the remote module through the information collection devices, including information actively provided by the user and information collected automatically, is transmitted to at least one analysis module, said analysis module is responsible for storage and computational processing of said information, generating a headache diagnosis for the user, together with at least one treatment suggestion. Alternatively, the system can provide more than one diagnosis and more than one treatment suggestion. The transmission of this information from a remote module to an analysis module takes place through network connections, including virtual private network (VPN), local (LAN), metropolitan (MAN), regional (RAN) or worldwide (WAN), preferably through the WAN type, more particularly through the internet.

In the context of the present invention, the term "remote module" refers to a computer or any other device with the means to collect, store, process and transmit information through a computer network, and may assume a plurality of configurations, including smartphones, tablets, notebooks, desktops, digital totems. According to an alternative embodiment of the present invention, the analysis module may assume the form of a computer network with means to carry out operations through cloud computing, that is, in a decentralized way. Alternatively, the configuration of the computer network that makes up the remote module can take on several architectures, including architectures of peer-to-peer systems, public blockchain, permissioned and semi-permissioned private blockchain, centralized network and decentralized network.

According to a preferred embodiment of the present invention, the computational analysis process carried out by the analysis module utilizes at least one computational algorithm and is preferably organized in a manner that comprises at least four distinct steps. At the end of the last step, the remote module will determine at least one medical diagnosis and a probability associated with its reliability and, at least, one medical treatment option for the diagnosed disease and a probability associated with said treatment effectiveness. In addition, this analysis module comprises a plurality of databases, including specific databases for the following types of information: medical professionals, medical treatments, types of headache, diseases associated with headache and medical examinations. Alternatively, such information stored in the databases of said analysis module is obtained through external databases, said analysis module being connected with such external databases through a network, including virtual private networks (VPN), local (LAN), metropolitan (MAN), regional (RAN) or worldwide (WAN), preferably via the WAN type, more particularly via the internet.

According to the same previous embodiment, the analysis module comprises means to execute computational processes based on the use of computational algorithms to optimize several aspects related to the functioning of the headache management system as a whole. Among these aspects are included: information collection procedures executed by the remote module, processes involved in the different steps of the computational diagnostic carried out by the analysis module and treatment suggestion for diagnosed diseases.

Within the scope of the present invention, the term "computational algorithm" indicates: any computational methods that comprise a finite sequence of actions, aimed at solving a problem or performing a given task.

In the context of the present invention, the term "probability" associated with the reliability of a diagnosis indicates: a numerical value that provides information about the probability of a given diagnosis being correct. Such numerical probability value can be expressed according to different types of values, such as E-values, P-values and may even be calculated by different statistical methods, such as Fisher, Neyman-Pearson, Bayes, relative risk, odds ratio.

In the context of the present invention, the term "medical treatment" indicates: any forms of medical treatment scientifically proven and approved to promote a person's clinical improvement, including acute treatment methods and preventive treatment methods. The term "acute treatment" indicates: medical treatments, preferably involving the administration of drugs, whose purpose is to interrupt the symptoms of a headache episode as soon as the person begins to experience the first symptoms. The term "preventive treatment" indicates: medical treatments, preferably through the administration of drugs, which aims to reduce the number, intensity and prevent the occurrence of headache episodes experienced by a person, being preferably recommended in severe cases.

Within the scope of the present invention, the term "effectiveness" associated with a treatment indicates a numerical value of a predictive character associated with the chance of success of a given medical treatment, that is, its chance of being effective in the treatment of a certain disease.

In accordance with the present invention, computational processing of information received from remote modules and performed by a computational module includes: a screening step; a headache diagnosis step; a comorbidities and associated factors assessment step; and an access and impact assessment step; wherein, after carrying out the headache diagnosis step, comorbidity and associated factors assessment step or access and impact factors assessment step, the system issues at least one medical diagnosis and a probability associated with its reliability and, at least, at least, a medical treatment option for the diagnosed disease associated with said treatment effectiveness. Additionally, the data received by the analysis module is preferably subjected to a pre-treatment, in which the data format is adapted or converted it into another type of information.

According to a preferred embodiment of the present invention, the data received by the analysis module undergoes a pre-treatment prior to the mentioned computational processing steps. During said pre-treatment, the information is properly formatted and converted into another information type. During pre-treatment, all information is preferably transformed into types such as numerical data, or any other form of data that can be easily processed, stored, combined, normalized and analyzed by the analysis module. In the specific case of audio information coming from voice, the pre-treatment performed by the analysis module may include extraction of information related to voice intensity, use of language and voice pattern, wherein said information may be processed by methods including Latent Semantics Analysis (LSA). In the specific case of facial and body image information, the pre-treatment carried out by the analysis module may include the extraction of information related to facial expression and pupil dilation. In the specific case of infrared facial image information, the pre-treatment carried out by the analysis module may include the extraction of information related to facial thermography. Alternatively, procedures carried out in the pre-treatment step may be carried out according to the steps disclosed as follow.

A screening step 101 comprises at least three questions designed to identify urgency and/or severity of the user's condition, including questions to assess whether the user has ever had a headache in life, the frequency of headache episodes in the last 12 months and in the last month; in which the term "headache episode" referring to a day on which headache was experienced at least once. If the user reports more than 15 headache episodes in the last month, a high severity alert is triggered to that user, and said alert is further used in other diagnostic steps, particularly when choosing the appropriate treatment, favoring preventive treatments over acute treatments.

A headache diagnosis step 102 comprises a headache diagnostic module 22, which is divided into at least two submodules, a primary headache diagnostic sub-module and a secondary headache diagnostic sub-module. The computational processing carried by the respective submodules is preferably executed simultaneously, or may be alternatively arranged in sequence, starting with the execution of the secondary headache diagnostic sub-module followed by the execution of the primary headache sub-module, or vice versa. The information analyzed in this step includes information on medical history, headache history, habits and addictions, in particular including information such as: alcohol consumption, trauma, allergies, seasonal (relative to the variation in the occurrence over the periods of the year), medications in use, menstruation (onset, end, intensity, associated symptoms), diagnosed diseases, presence of aura associated with headache, pain location, prodromes associated with headache, frequency of headache episodes, photophobia, phonophobia and odor discomfort.

Within the scope of the present invention, the term "primary" associated with headache or diseases indicates: headaches such as migraine, tension headache, trigeminal-autonomic headache, cluster headache, headache present in chapters 1 to 4 of the international headache classification.

Within the scope of the present invention, the term "secondary" associated with headache or diseases indicates: headaches that are part of a symptom of some other disease such as tumors, infections, circulatory, metabolic changes, by ingestion or withdrawal of some substance.

The secondary headache diagnostic sub-module evaluates user information collected by the remote module based on the secondary headache diagnosis criteria. These criteria are based on the diagnosis guidelines established by chapters 5 to 13 of the International Classification of Headache Disorders published by the International Headache Society. By the end of the criteria evaluation, if a secondary headache has been identified, the analysis module requests further exams to improve diagnosis or suggests further consultations with professionals with a specific expertise. Before requesting further examinations, the analysis module must identify the absence or insufficiency of information for high reliability secondary headache diagnosis. The requested exam is chosen from the exam options stored in the analysis module medical exam database. In turn, the appointment of a medical professionals is made based on the medical profiles stored in the analysis module database.

In the context of the present invention, the term "high reliability" indicates: a probability value associated with the reliability of a treatment whose numerical value is considerably high, more specifically a probability value above 50%.

The primary headache diagnostic sub-module evaluates user information collected by the remote module based on the primary headache diagnosis criteria. The diagnosis criteria implemented by said primary headache module classifies headache into four major groups, including: migraines, tension headache, trigeminal-autonomic and others. These criteria are based on the diagnosis guidelines established by chapters 1 to 4 of the International Classification of Headache Disorders published by the International Headache Society. By the end of the criteria evaluation, if the patient's information matches a primary headache category criterion, the analysis module diagnoses the headache as said category. Once the diagnosis is determined, the module suggests at least one treatment option for the user, among the medical treatments stored in the analysis module medical treatment database.

According to the preferred embodiment of the present invention, once the diagnosis of a headache has been determined and a treatment has been suggested for the user, the system provides means for the evolution and monitoring of disease progression and effectiveness of the treatment suggested. The monitoring process includes periodic collection of information through a remote module and collection devices, through which the user may report the improvement, worsening or any other changes in his well-being, health and/or quality of life. If the patient registers an improvement in his well-being, health and/or quality of life successively over a given period, the system may make available an option to interrupt treatment monitoring. Within the scope of the present invention, said "given time" necessary for the treatment monitoring interruption to be available, may be determined according to different criteria, including: a 50% drop in the number of headache episodes, preferably at least 70% drop, more preferably 80%, even more preferably 95%. On the other hand, if the user does not experience improvements during the monitoring period, the system will identify the treatment as ineffective, triggering the initiation of the comorbidity and associated factors assessment step. Alternatively, prior to the initiation of a comorbidity and associated factors assessment step, the analysis module may suggest an alternative second treatment among those stored in the analysis module medical treatment database. The decision whether to start the alternative second treatment or the comorbidity and associated factors assessment step is up to the user.

According to a preferred embodiment of the present invention, the diagnoses communication, treatment suggestions, medical professionals appointment and any other information to be communicated to the user, are provided through a remote module or other means of communication, including email, message or phone call.

The comorbidity and associated factors assessment step 103 involves the analysis of information on medical history, headache history, habits and addictions and other symptoms and pain, wherein said information is analyzed in relation to the headaches reported by the user. As a result, at least one medical diagnosis and a probability associated with the diagnosis reliability are presented, and at least one medical treatment for said diagnosed disease and a probability associated with said treatment effectiveness, wherein said medical treatment is chosen from medical treatments stored in the analysis module medical treatment database. More specifically, this step involves the analysis of the following information: medications in use, health diagnosis, headache-related comorbidities, weight, height, BMI, auditory impedanciometry, blood pressure, oximetry, body temperature, mental health (including traumatic events), anxiety, depression, compulsion, attention deficit, hyperactivity, personality, optimism, pessimism), allergies (including rhinitis, sinusitis, dermatitis, asthma), hormonal profile, gynecological health (concerning the balance of female sex hormones and reproductive structures), metabolic profile, digestive profile, other body pains, quality of sleep, routines related to sleep and rest, drug use, alcohol use, smoking, food, physical activity.

According to the preferred embodiment of the present invention, the choice of a medical treatment for a given disease diagnosed by the system involves analyzing the effectiveness criteria associated with each of the treatments stored in the module analysis medical treatment database. Among the criteria associated with each treatment, at least one of the following criteria is included: efficacy, therapeutic gain, number needed to treat (NNT), tolerability, number needed to harm (NNH), efficacy/tolerability ratio and NNT/NNH.

In the context of the present invention, the term "efficacy" associated with a treatment indicates improvement in clinical outcomes with a given intervention.

In the context of the present invention, the term "therapeutic gain" associated with a treatment indicates the total effectiveness of the intervention minus the placebo effect.

In the context of the present invention, the term "number needed to harm (NNH)" associated with medical treatment indicates: the average number of people undergoing a given treatment required for person in average to suffer health damage, wherein said damages would not have been caused had the person not been subjected to said treatment.

In the context of the present invention, the term "number needed to treat (NNT)" associated with medical treatment indicates: the average number of people undergoing a given treatment required for one person in average to prevent health damage (with respect to a control group in clinical trials), wherein said damage prevention would not have happened had the person not been subjected to said treatment.

In the context of the present invention, the term "tolerability" associated with a treatment indicates the degree of side effects due to a given treatment.

An access and impact factor assessment step 104 comprises the analysis of access and impact information and medical history in order to provide at least one treatment option more suitable to the user, taking into account additional factors for delimitation.

According to a preferred embodiment of the present invention, the computational processing of information carried out by the analysis module is based on a decision tree type computational algorithm. Within the scope of the present invention, the decision tree may be based on a plurality of types of decision tree algorithms, including bootstrap, bootstrap aggregation, random forest, and markov.

According to the same preferred configuration above, the analysis module makes use of computational tools, in particular neural networks and machine learning, in the execution of several of its decisions, including the determination of probability associated with the diagnosis reliability, the effectiveness determination associated with a given treatment suggested by the analysis module, determination of primary and secondary headache diagnoses. In addition, the present invention discloses the use of said computational tools in order to produce headache diagnosis classifications with respect to the types of treatment proven effective for a given type of headache. Such classification takes into account all the information collected about the users registered in the system and the types of treatments that have proven to be effective for each patient, allowing for the identification of particularly relevant information in the production of classifications which are correlated with greater effectiveness of certain types of treatment. With this, the present system provides means to store such classifications and use them as an additional criterion to suggest headache treatments with greater effectiveness. It is worth mentioning that, the procedure for readjusting these classifications is continuous, causing the classifications to become more and more refined over time, making them powerful clinical tools. The use of such disease classifications enables the present invention to achieve better results in headache treatment when compared to the methods disclosed in the state of the art. Furthermore, the implementation of additional information to those disclosed in the state of the art, such as facial expression, voice intensity, speech pattern, use of language, hand tremor, among others, allows the inference of subtle information, such as conditions or diseases related to mental health, which are difficult to collect, both for state of the art solutions and for the best trained medical professionals. Thus, the solution disclosed herein is highly inventive, having not been anticipated or suggested by the solutions contained in the state of the art.

According to the present invention, the neural network algorithm used by the system is structured so that the input information includes information collected by a remote module and further pre-treated by a remote or analysis module. Additionally, the information output includes at least one diagnosis and at least one medical treatment suggestion. The multiple hidden layers of said neural network are adjusted to optimize the diagnosis model and disease classification. The methods used to perform such optimization are known to those skilled in the art.

According to the present invention, neural network and/or machine learning algorithms include Bagging classifiers, SVM (support vector machine) classifiers, NC (node classifier), NCS (neural classifier system), SCRLDA (Shrunken Centroid Regularized Linear Discriminate and Analysis), Random Forest; Naiive Bayes; aggregating bootstrap; boosting; LASSO; minimum-redundancy maximum-relevancy (mRMR) and/or any combinations thereof.

Figure 1:
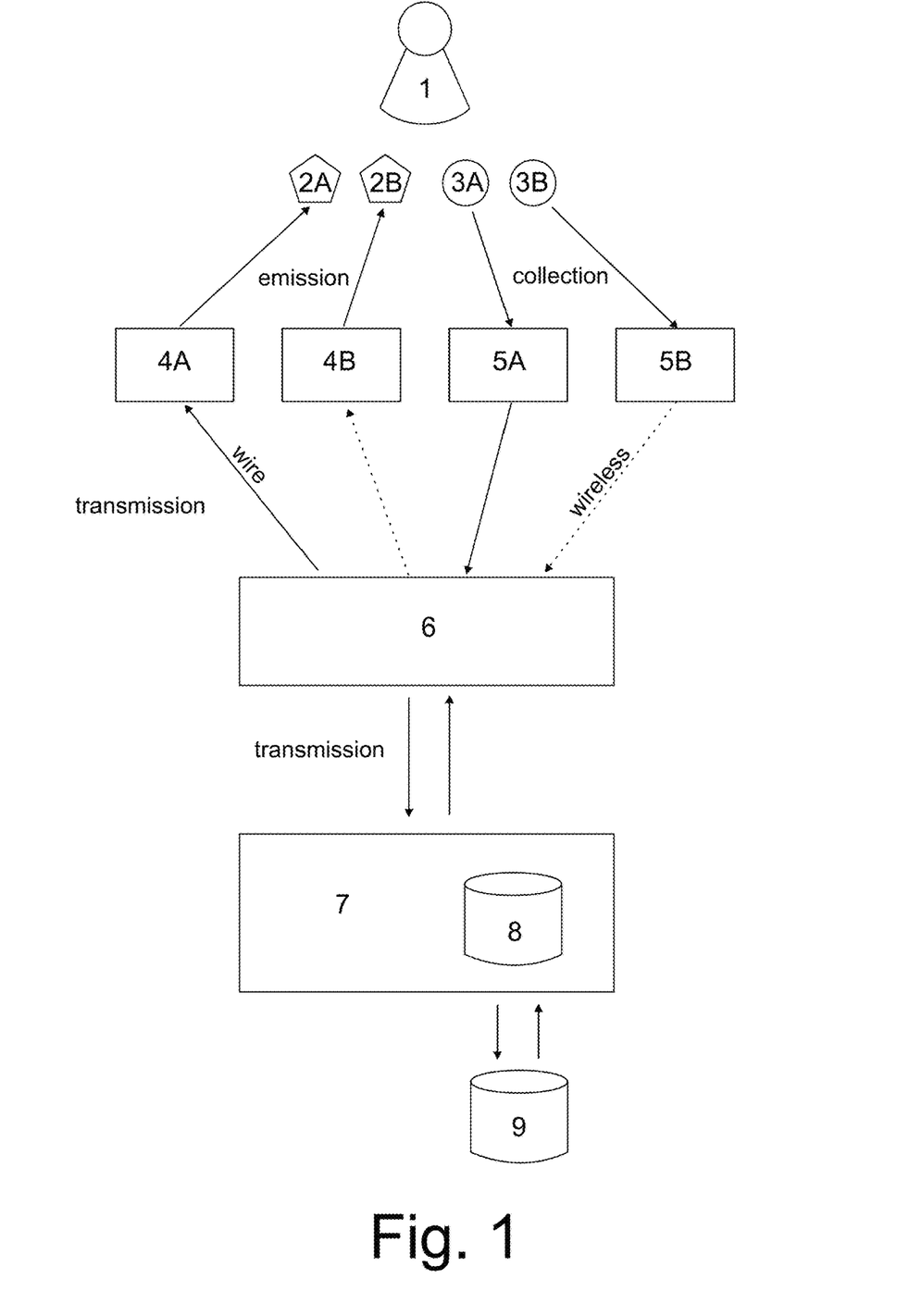
FIG. 1—Illustration of an embodiment of the physical components of the intelligent management system.

According to the preferred embodiment illustrated in FIG. 1, the intelligent headache diagnosis system comprises a plurality of remote modules 6, which in turn comprises a plurality of collection devices 5 and stimulus devices 4, and at least an analysis module 7; said remote modules 6 are connected with at least one analysis module 7 comprising at least one internal database and said analysis module 7 is optionally connected to at least one database external 9. Said remote module 6 is configured as the main interface of interaction with user 1, with which it will establish interaction through stimulus devices 4A, 4B, and said devices have means for the emission of sensory stimuli 2A, 2B, and using collection devices 5A, 5B with means to collect information 3A, 3B from user 1 through automatic collection or by the active provision of information 3A, 3B by user 1. Once collected, information 3A, 3B is transmitted from the remote module 6 for analysis module 7, where they are computationally processed.

Figure 2:
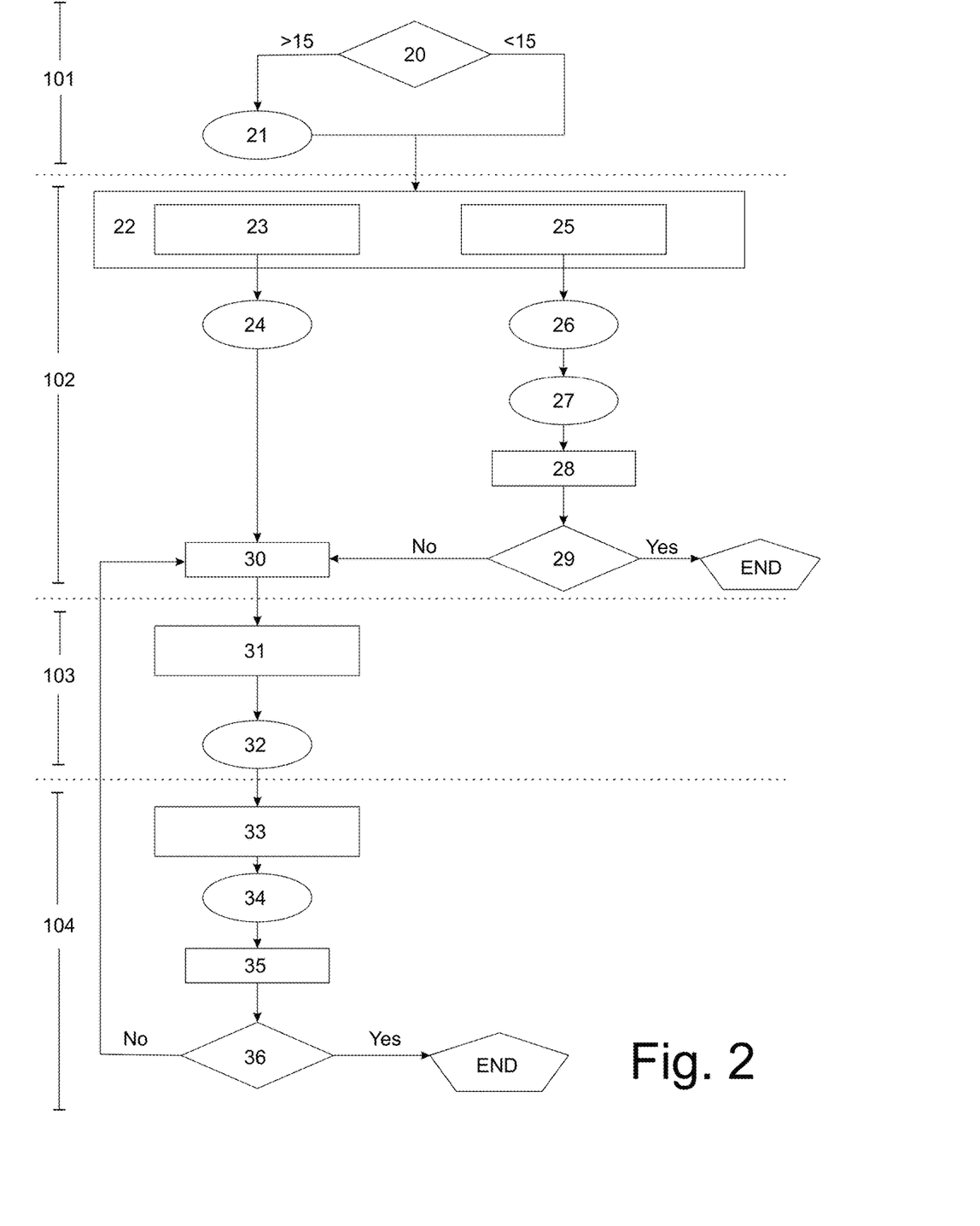
FIG. 2—Preferred embodiment of the computational processing performed by the analysis module of the present invention.

According to the preferred embodiment illustrated by FIG. 2, the computational processing carried out by said analysis module 7 comprises at least four stages of analysis 101, 102, 103 and 104, or equivalent, including the following steps: screening 101; diagnosis of headache 102; comorbidity and associated factors assessment 103; access and impact factors assessment 104.

Initially, a screening step 101 is carried with the objective of initially assessing the apparent severity of the user's clinical condition 1. Such assessment is made by means of a brief questionnaire on the frequency of headache episodes 20, which may result or not in a high-severity alert 21.

In the next moment, a headache diagnosis step 102 is carried out to diagnose a headache disorder and suggest and monitor a medical treatment. In this step, the information collected from the patient is processed by a headache diagnosis module 22, which comprises at least two distinct sub-modules, a primary headache sub-module 25 and one for secondary headache sub-module 23. If it is identified that the user match the secondary headache criteria, the system will provide a diagnosis of secondary headache 24. In case of verification of insufficient information to identify the primary cause associated with secondary headache, the system will provide recommendations 30 for new medical examinations or appoint further medical appointment with a medical specialist. If the patient is matches the primary headache criteria, the system will provide at least one diagnosis of primary headache 26 and at least one medical treatment 27 for the diagnosed primary headache 26. Once the patient accepts and begins one of the suggested treatments 27, the treatment monitoring 28 begins. Said treat monitoring 28 aims to evaluate the headache and treatment effectiveness 27. The information collected during said treatment monitoring 28, enables the system to perform a treatment success assessment 29. If the treatment has been considered effective, the user has the option to stop the treatment. If treatment is found to be ineffective, the system will provide recommendations 30 for further medical examinations or appoint for further medical consultations with a medical specialist, in order to improve the quality and precision of the diagnosis.

The next step is the comorbidity and associated factors assessment. This step aims to improve the diagnosis through the analysis of user information that potentially contributes to the headache occurrence. The computational processing of this step is carried out by an evaluation module for comorbidity and associated factors 31, which results in an improved diagnosis 32.

At last, a fourth access and impact factors assessment step are executed, aiming to further refine the selection of an appropriate treatment for a given disease. The computational analysis of this step is carried by an access and impact factors module 33, which outputs at least one treatment for the improved diagnosis 32. Once the patient accepts and begins one of the suggested treatments 34, the treatment monitoring 35 begins in order to assess the evolution of headache and treatment effectiveness 34. The information collected during treatment monitoring 35, enables the system to execute a treatment success evaluation 36. If the treatment is considered effective, the user has the option to end treatment. If the treatment is found to be ineffective, the system will provide recommendations 30 for further medical examinations or further medical consultation with a specialist, in order to improve the diagnosis.

Still according to another preferred embodiment of the present invention, the system enables the registration of a plurality of types of users, including: people who are seeking medical assistance, either to obtain a diagnosis or get medical instructions, such as treatment and exam suggestions and/or further medical specialist appointment; medical professionals who seeking access to their patients' information; company administrators seeking access to medical information, such as diagnostic reports of their employees; life insurance providers or health plans seeking access to their clients' medical information. The access of information of a given user by third parties, such as doctors, company administrators, companies providing life insurance and health plans, will only be allowed with the authorization of the user himself, wherein the remote module comprises means to grant such authorization.

The present invention is not limited by the embodiments disclosed herein. Alternative embodiments proposed by those skilled in the art are also included in the scope of the present invention.

The invention claimed is:

1. AN INTELLIGENT HEADACHE MANAGEMENT SYSTEM comprising:
a plurality of remote modules; and
at least one analysis module,
wherein said plurality of remote modules are connected with the at least one analysis module, wherein said plurality of remote modules are responsible for a collection of information related to the user, and said collection of information is carried out by at least one information collection device connected to said plurality of remote modules, and said information is transmitted to the at least one analysis module, wherein said at least one analysis module has a database configured to store and to perform computational processing of the information transmitted by a remote module of the plurality of remote modules thereby producing results of the computational processing of said information, and the results of the computational processing of said information are transmitted to the plurality of remote modules, where said results are made available to the user;
wherein said remote module of the plurality of remote modules comprises the at least one information collection device for collection of information actively provided by the user and for automatic collection of information from the user, said remote module of the plurality of remote modules comprising at least one stimulus device configured to emit a sensory stimuli in order to provoke biological responses from the user, wherein said biological responses are automatically collected through the at least one information collection device.

2. THE INTELLIGENT HEADACHE MANAGEMENT SYSTEM according to claim 1, wherein the information of the user which are automatically collected by the devices connected to the remote module of the plurality of remote modules includes at least one of the following types of information:
a) voice audio;
b) heartbeat;
c) facial and body image;
d) infrared facial image;
e) auditory impedance information;
f) blood pressure information;
g) body temperature;
h) oximetric information;
i) hand tremor;
j) electroencephalographic information.

3. THE INTELLIGENT HEADACHE MANAGEMENT SYSTEM according to claim 1, wherein said remote module of the plurality of remote modules comprises at least one of the following information collection devices:
a) microphone;
b) heart rate sensor;
c) digital camera;
d) infrared camera;
e) impedanciometer;
f) digital sphygmometer;
g) thermometer;
h) oximeter;
i) accelerometer;
j) helmet or cap for electroencephalogram;
k) touchscreen panel.

4. THE INTELLIGENT HEADACHE MANAGEMENT SYSTEM according to claim 1, wherein said remote module of the plurality of remote modules comprises the at least one stimulus device configured to emit at least one of the following types of sensory stimuli:
a) visual;
b) olfactory;
c) auditory;
the emission of visual stimuli is carried out by an image reproduction device;
the emission of olfactory stimuli is carried out by an odor release device; and
the auditory stimuli emission is carried out by a sound reproduction device.

5. THE INTELLIGENT HEADACHE MANAGEMENT SYSTEM according to claim 4, wherein the automatic collection of information related to the biological response from the user, carried out by at least one information collection device connected to the remote module of the plurality of remote modules, is initiated immediately after the emission of sensory stimulus, said stimulus being emitted by at least one stimulus device.

6. THE INTELLIGENT HEADACHE MANAGEMENT SYSTEM according to claim 5, wherein said emitted stimulus is a visual stimulus.

7. THE INTELLIGENT HEADACHE MANAGEMENT SYSTEM according to claim 5, wherein said emitted stimulus is an olfactory stimulus.

8. THE INTELLIGENT HEADACHE MANAGEMENT SYSTEM according to claim 5, wherein said emitted stimulus is an auditory stimulus.

9. THE INTELLIGENT HEADACHE MANAGEMENT SYSTEM according to claim 5, wherein said emitted stimulus comprises at least two types of sensory stimuli choose from: visual, olfactory and auditory.

10. THE INTELLIGENT HEADACHE MANAGEMENT SYSTEM according to claim 1, wherein the information collected automatically after the start of stimulus emission includes at least one of the following information:
a) voice audio;
b) heartbeat;
c) facial and body image;
d) infrared facial image;
e) auditory impedance information;
f) blood pressure information;
g) body temperature;
h) oximetric information;
i) hand tremor;
j) electroencephalographic information.

11. THE INTELLIGENT HEADACHE MANAGEMENT SYSTEM according to claim 1, wherein said at least one information collection device is configured to quantitatively measure the degree of photophobia, phonophobia and odor discomfort, said measurement involves collecting information obtained by information collection devices connected to the remote module of the plurality of remote modules, and is configured to computationally process said information in an analysis module, wherein said collected information comprises voice audio information and facial and body image, and wherein said information is converted by said analysis module into at least an information related to voice intensity, use of language, speech pattern, facial expression and pupil dilation, said information being further transformed in numerical information and computationally processed to define the degree of phonophobia, photophobia and odor discomfort.

12. THE INTELLIGENT HEADACHE MANAGEMENT SYSTEM according to claim 1, wherein the information received by the analysis module is computationally processed, and wherein said processing comprises at least the following four steps:
a) a screening step;
b) a headache diagnosis step, performed by a headache diagnosis module, said module being divided into at least two distinct diagnostic submodules, the at least two distinct diagnostic submodules including a first primary headache submodule and a second secondary headache submodule;
c) a comorbidities and associated factors assessment step; and
d) an access and impact assessment step;
the screening step involving a questionnaire about the frequency of headache episodes, and in case of a weekly frequency response greater than or equal to 15 episodes, a high severity alert is triggered in the system;
the headache diagnosis step involving the analysis of user information, including information actively provided by the user and information collected automatically, including information on medical history, headache history, habits and addictions, wherein the analysis of this stage is performed in two diagnostic submodules, the first primary headache submodule and the second secondary headache diagnostic submodule;
the comorbidities and associated factors assessment step involving the analysis of a plurality of user data, including information on medical history, headache history, habits and addictions and other symptoms and pains, and this analysis being carried out by a comorbidities and associated factors assessment module;
the access and impact assessment step involves the analysis of information about access and impact and medical history, being said analysis carried out by an access and impact assessment module.

13. THE INTELLIGENT HEADACHE MANAGEMENT SYSTEM according to claim 12, wherein the analysis module is configured to store and process the information collected by the remote module of the plurality of remote modules, wherein processing of said information involves the use of computational decision tree algorithms, the result of said analysis comprises a diagnosis of at least one disease associated with a probability associated with the reliability of said diagnosis and a recommendation of at least one medical treatment associated with its effectiveness in the treatment of said diagnosed disease, said treatment being chosen from those stored in a analysis module treatment database.

14. THE INTELLIGENT HEADACHE MANAGEMENT SYSTEM according to claim 12, wherein the computational processing carried out by the analysis module uses at least one decision tree algorithm.

15. THE INTELLIGENT HEADACHE MANAGEMENT SYSTEM according to claim 12, wherein the decision tree algorithm used comprises at least one of the following algorithm types: bootstrap, bootstrap aggregation, random forest, and markov.

16. THE INTELLIGENT HEADACHE MANAGEMENT SYSTEM according to claim 12, wherein the information collection procedure carried out by the remote module of the plurality of remote modules and the decision tree algorithm executed by the analysis module are constantly optimized through the implementation of computational tools based on machine learning and neural networks.

* * * * *